(12) United States Patent
Sughrue et al.

(10) Patent No.: US 11,581,082 B2
(45) Date of Patent: Feb. 14, 2023

(54) SUBSETTING BRAIN DATA

(71) Applicant: Omniscient Neurotechnology Pty Limited, Queens Park (AU)

(72) Inventors: Michael Edward Sughrue, Sydney (AU); Stephane Philippe Doyen, Glebe (AU); Xinling Jiang, Willoughby (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 25 days.

(21) Appl. No.: 16/875,786

(22) Filed: May 15, 2020

(65) Prior Publication Data
US 2021/0358592 A1 Nov. 18, 2021

(51) Int. Cl.
*G16H 20/40* (2018.01)
*G16H 50/20* (2018.01)
*G16H 30/20* (2018.01)
*G16H 10/60* (2018.01)

(52) U.S. Cl.
CPC ............. *G16H 20/40* (2018.01); *G16H 10/60* (2018.01); *G16H 30/20* (2018.01); *G16H 50/20* (2018.01)

(58) Field of Classification Search
CPC .................. G06Q 50/22–24; G06Q 50/20–26
See application file for complete search history.

(56) References Cited

U.S. PATENT DOCUMENTS

| | | | | |
|---|---|---|---|---|
| 5,869,336 A * | 2/1999 | Meyer | ................. | C12N 9/6472 435/348 |
| 11,188,850 B2 * | 11/2021 | Pisner | ................. | G06F 9/4881 |
| 2009/0062623 A1 * | 3/2009 | Cohen | ................. | G16H 70/60 600/300 |
| 2015/0023556 A1 | 1/2015 | Kim et al. | | |
| 2015/0272461 A1 * | 10/2015 | Morimoto | ............. | A61B 5/316 600/410 |
| 2017/0000422 A1 * | 1/2017 | Moturu | ................ | A61B 5/0022 |
| 2017/0177822 A1 * | 6/2017 | Fogel | .................... | G16H 50/20 |
| 2017/0188932 A1 | 7/2017 | Singer et al. | | |
| 2018/0098738 A1 | 4/2018 | Sutoko et al. | | |
| 2019/0167179 A1 | 6/2019 | Arzy | | |
| 2020/0160985 A1 * | 5/2020 | Kusuma | ................ | G16H 30/40 |

(Continued)

OTHER PUBLICATIONS

"Connectivity." Apr. 5, 2019. The Virtual Brain. (Year: 2019).*

(Continued)

*Primary Examiner* — Neal Sereboff

(74) *Attorney, Agent, or Firm* — Fish & Richardson P.C.

(57) ABSTRACT

Methods, systems, and apparatus, including computer programs encoded on computer storage media, for determining a subset of brain data of a patient. One of the methods includes obtaining data characterizing a brain of a patient; determining a first prompt for presentation to a user; obtaining a first user input characterizing a first response to the first prompt; determining, using the first response to the first prompt, a second prompt for presentation to the user; obtaining a second user input characterizing a second response to the second prompt, wherein at least one of the first prompt or the second prompt seek a response based on a clinical observation of the patient; and determining a subset of the obtained data using the first response to the first prompt and the second response to the second prompt.

19 Claims, 9 Drawing Sheets

(56) References Cited

U.S. PATENT DOCUMENTS

| | | | | |
|---|---|---|---|---|
| 2020/0167694 A1* | 5/2020 | Pisner | .................... | G06F 9/4881 |
| 2020/0211716 A1* | 7/2020 | Lefkofsky | .............. | G16H 10/60 |
| 2021/0090694 A1* | 3/2021 | Colley | .................... | G16B 40/00 |
| 2021/0342655 A1* | 11/2021 | Vigh | ..................... | G06K 9/6289 |

OTHER PUBLICATIONS brainiak.org, [online] "Brain Imagining Analysis Kit" retrieved on May 27, 2020, retrieved from URL <https://brainiak.org/>, 2017, 2 pages.

Fissell, "Workflow-Based Approaches to Neuroimaging Analysis," Methods in Mol. Biol., 2007, 401:435-266.

mlnl.cs.ucl.ac.uk [online], "Pattern Recognition for Neuroimaging Toolbox (PRoNTo)" retrieved on May 27, 2020, retrieved from URL <http://www.mlnl.cs.ucl.ac.uk/pronto/index.html>, 2018, 2 pages.

thevirtualbrain.org, [online] "Understanding what counts: The key to make brain simulation feasible," retrieved on May 27, 2020, retrieved from URL <https://thevirtualbrain.org/tvb/zwei/neuroscience-simulation> 2017, 8 pages.

Vincent et al., "MNI Display—Software for Visualization and Segmentation of Surfaces and Volumes," Montreal Neurological Institute and Hospital, Jun. 26, 2016, 50 pages.

Waller et al., "GraphVar 2.0: a user-friendly toolbox for machine learning on functional connectivity measures," J. Neurosci. Meth., Oct. 2018, 38:21-33.

Becker et al., "Going Beyond Diffusion Tensor Imaging Tractography in Eloquent Glioma Surgery—High-Resolution Fiber Tractography: Q-Ball or Constrained Spherical Deconvolution?" World Neurosurg., Feb. 2020 134:e596-609.

Bonney et al., A Simplified Method of Accurate Postprocessing of Diffusion Tensor Imaging for Use in Brain Tumor Resection, Oper Neurosurg (Hagerstown) 13, 47-59 (2017).

Burks et al., "A method for safely resecting anterior butterfly gliomas: the surgical anatomy of the default mode network and the relevance of its preservation". J. Neurosurg., Sep. 2016, 126(6):1795-811.

Dell'Acqua and Tournier, "Modelling white matter with spherical deconvolution: How and why?" NMR Biomed., 2019, 32:e3945.

Fan et al., "The Human Brainnetome Atlas: A New Brain Atlas Based on Connectional Architecture," Cereb Cortex, 2016, 26:3508-26.

Fischl, "FreeSurfer," Neuroimage, 2012, 62:774-81.

Garyfallidis et al., "Dipy, a library for the analysis of diffusion MRI data," Frontiers in Neuroinformatics, 2014. 8:1-17.

Glasser et al., "A multi-modal parcellation of human cerebral cortex," Nature, 2016, 536:171-8.

Glenn et al., "Common Disconnections in Glioma Surgery: An Anatomic Description," Cureus, 2017, 9:e1778.

Ille et al., Functional Reorganization of Cortical Language Function in Glioma Patients—A Preliminary Study. Frontiers in Oncology 9 (2019).

Jin et al., "Functional and anatomical connectivity-based parcellation of human cingulate cortex." Brain Behav., 2018, 8:e01070.

Ohue et al., "Evaluation of intraoperative brain shift using an ultrasound-linked navigation system for brain tumor surgery," Neurol. Med. Chir., 2010, 50:291-300.

Panesar et al., "Tractography for Surgical Neuro-Oncology Planning: Towards a Gold Standard." Neurotherapeutics, 2019, 16:36-51.

Rijnen et al., "Cognitive functioning in patients with low-grade glioma: effects of hemispheric tumor location and surgical procedure" 2019, 1(4):81-99.

Smilha et al., "Resting state fMRI: A review on methods in resting state connectivity analysis and resting state networks," Neuroradiol. J., 2017, 30:305-17.

PCT International Search Report and Written Opinion in International Appln. No. PCT/AU2021/050346, dated May 28, 2021, 9 pages.

Author: Derek Pisner Title of Publication: PyNets Page(s) being submitted: Claim chart with URL hyperlinks to the relevant source code located on GitHub and dated Apr. 25, 2020, three weeks before the May 15, 2020 filing date of publication 16875786. Location of public-facing, open-source snapshot of the PyNets package dated Apr. 25, 2020: https://github.com/dPys/PyNets/tree/2fe9f51b4f046554c4170edab2036acf0b821690.†

\* cited by examiner
† cited by third party

What would you like to accomplish? ✕

291 — Go to viewer
292 — Plan a surgery
293 — Research mode

290

< Back ✕
What region of the brain?

Medical frontal | Lateral frontal | Insula | Temporal lobe
Lateral parietal | Anterior occipital | Medical partietal | Occipital Lobe ◎ > Quickmind > Quick plan a surgery > What part of the brain?

294

< Back ✕
What disease are you interested in?

Brain tumor | Stroke | Dementia | Parkinsons
Depression | OCD | Epilepsy | I don't know let me freestyle ◎ > Quickmind > Use research mode > What disease are you interested in?

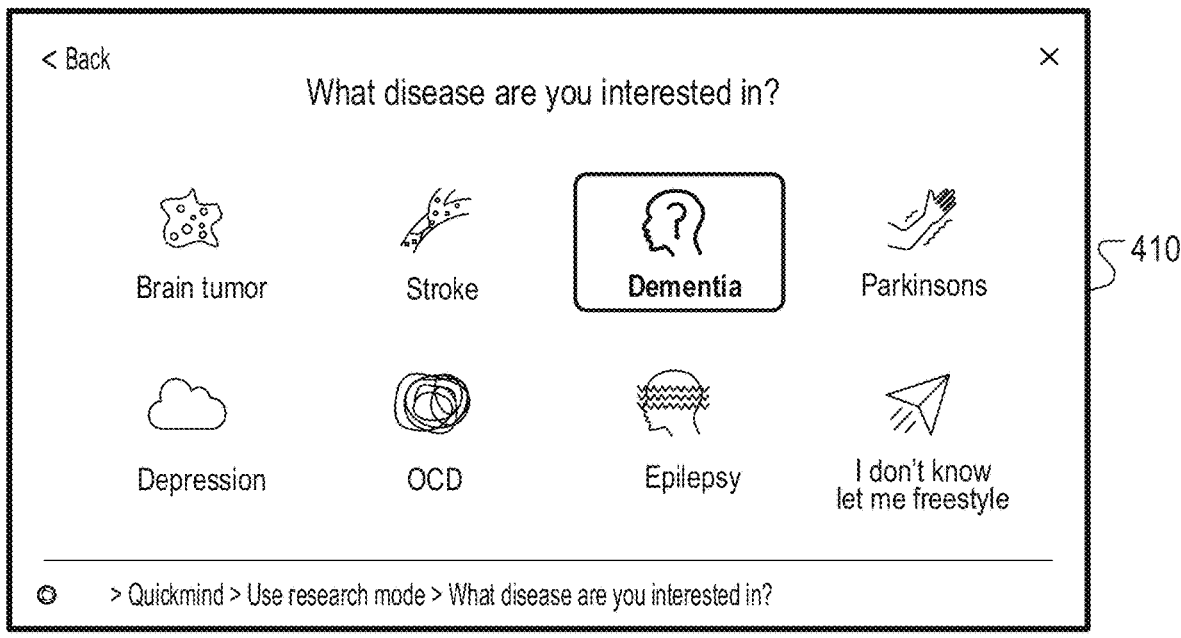
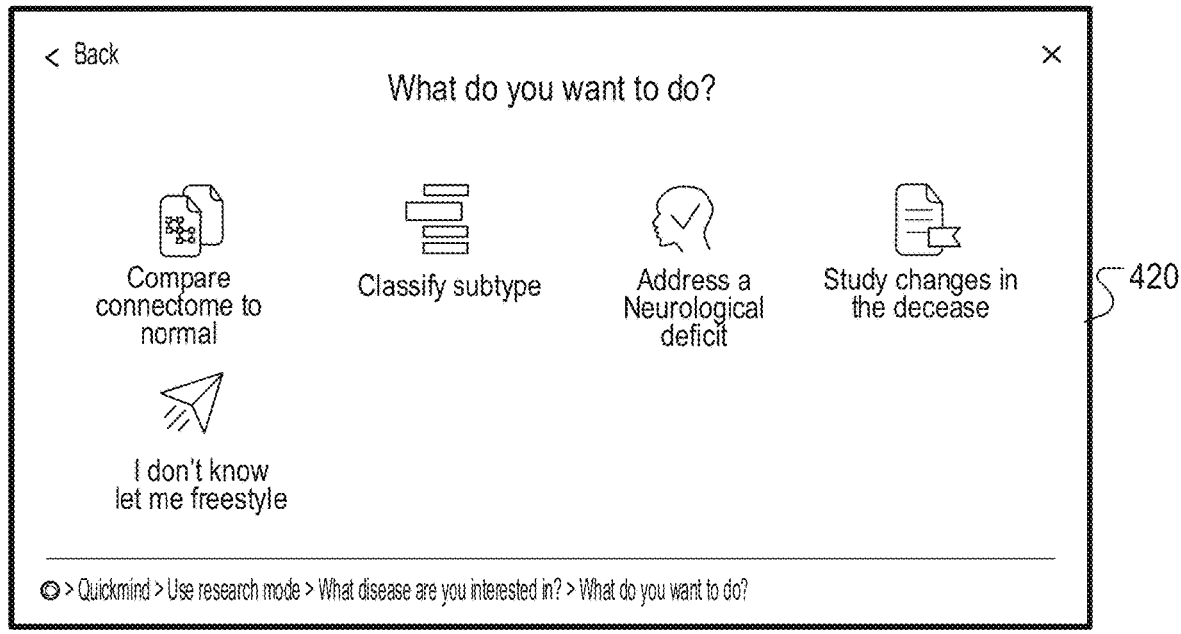
FIG. 4

FIG. 5

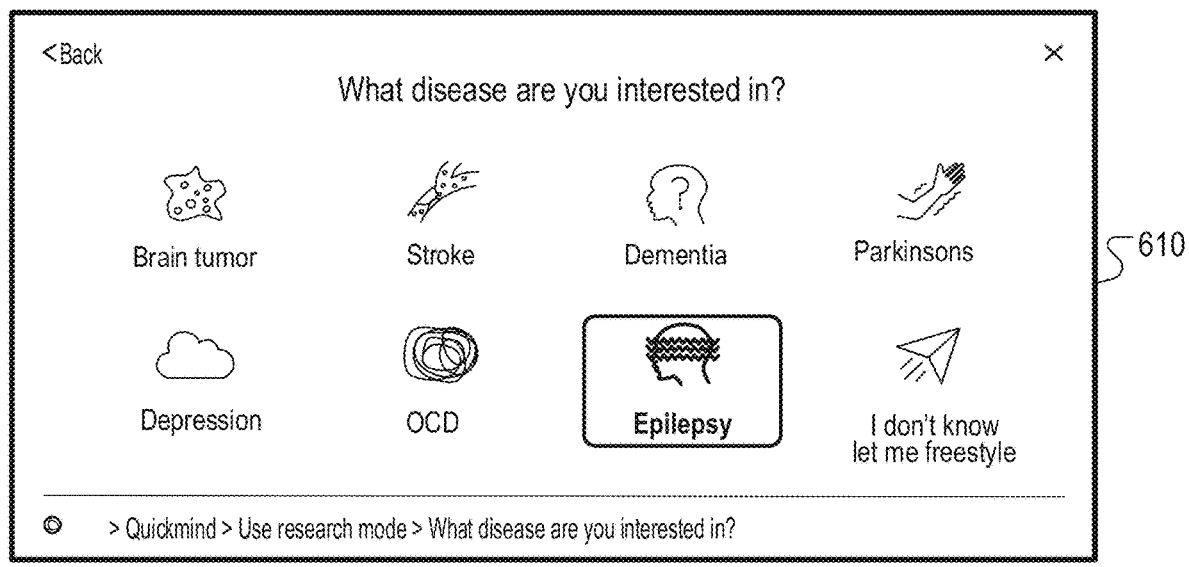
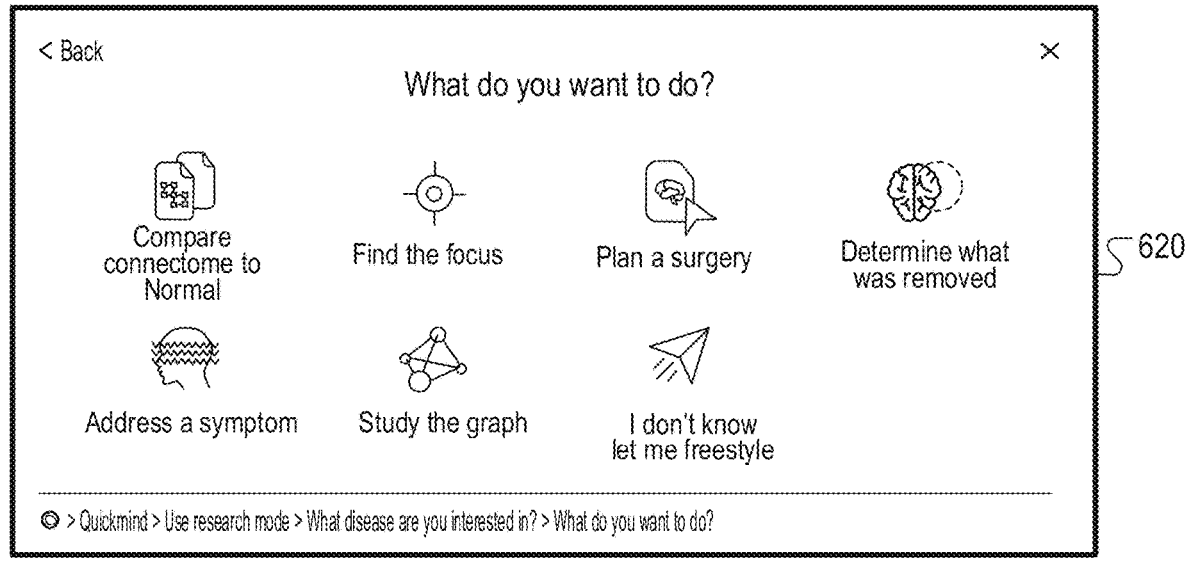
FIG. 6

SUBSETTING BRAIN DATA

BACKGROUND

This specification relates to processing data related to the brain of a patient, e.g., functional magnetic resonance imaging (MM) data and/or diffusion tractography data.

Brain functional connectivity data characterizes, for each of one or more pairs of locations within the brain of a patient, the degree to which brain activity in the pair of locations is correlated.

One can gather data related to the brain of the patient by obtaining and processing images of the brain of the patient, e.g., using magnetic resonance imaging (MM), diffusion tractography (DT) imaging, or functional MRI imaging (fMRT). Diffusion tensor imaging uses magnetic resonance images to measure diffusion of water in a human brain. One can use the measured diffusion to generate images of neural tracts and corresponding white matter fibers of the subject brain.

Data related to the brain of a single patient can be highly complex and high-dimensional, and therefore difficult for a clinician to manually inspect and parse, e.g., to plan a surgery or diagnose the patient for a brain disease or mental disorder. For example, a correlation matrix, e.g., a correlation matrix of fMRI data, of the brain of a patient can be a matrix with hundreds of thousands or millions of elements.

SUMMARY

This specification relates to determining a subset of brain data of a patient that is clinically relevant for the patient, e.g., a subset of brain data that is relevant to a diagnosable condition and/or upon which a user/clinician can take an action, and presenting the subset of the brain data to a user. For example, the system can determine a subset of the brain data that is clinically relevant for a particular brain disease or mental disorder, one or more symptoms, or a particular brain surgery that the patient may undergo. As a particular example, the system can determine a subset of fMRI data, e.g., correlation matrices, and diffusion tractography data characterizing the brain of the patient.

In this specification, brain data can be any data characterizing the brain of a patient. For example, brain data can include one or both of i) direct measurement data of the brain of the patient, e.g., images of the brain collected using brain imaging techniques, or ii) data that has been derived or generated from initial measurement data of the brain of the patient, e.g., correlation matrices.

In order to determine the subset of the brain data, a system can provide a series of prompts to the user corresponding to clinically-relevant questions about the patient. Upon receiving a response to a particular prompt, the system can either determine the subset of the brain data according to the received responses to the particular prompt and the previous prompts, or determine a next prompt to provide to the user. That is, the sequence of prompts can be dynamic according to the responses provided by the user.

Particular embodiments of the subject matter described in this specification can be implemented so as to realize one or more of the following advantages. As discussed above, a set of brain data characterizing the brain of a single patient can often be incredibly large and complicated, and thus it can be difficult and time consuming for a user to extract useful information from the set of brain data.

Using techniques described in this specification, a system can determine a subset of the brain data that is significantly smaller than the entire set of brain data, e.g., $\frac{1}{100}^{th}$, $\frac{1}{1,000}^{th}$, or $\frac{1}{10,000}^{th}$ the size of the entire set of brain data where the entire set represents all or most of the connections represented in a connectome (a map of neuronal connections in the brain). Therefore, the user is not forced to search through and analyze a large amount of data that is not relevant to the particular use case of the user, e.g., a particular disease or brain surgery. Rather, the system provides to the user the subset of the brain data that has been determined, either through clinical studies or by one or more machine learning models, to be clinically relevant for the particular use case.

Using techniques described in this specification, a system can determine a series of prompts that are to be provided to the user that allow the user to quickly navigate to a target subset of the data. As particular examples, the series of prompts can include only 2, 5, or 10 prompts to which the user can respond with relative ease. Therefore, the amount of time that a user must spend to discover the portion of the brain data that is useful to the user can be drastically reduced, resulting in improved outcomes for patients, users and/or clinicians, especially when effective care requires time sensitive investigations.

In some implementations, the system can further recommend one or more machine learning models for processing the determined subset of the brain data. The recommended machine learning models can be determined according to the same series of prompts by which the subset of brain data was determined, and can generate an output that is clinically relevant for the user. As a particular example, a recommended machine learning model can process the determined subset of the brain data to generate a prediction for whether the patient has a particular brain disease that was identified by the user in the responses to the series of prompts. Therefore, the system can provide immediate access to the most relevant machine learning models to the user, without requiring the user to select expressly the machine learning model(s) relevant to the context. This can be particularly advantageous when the system has a large library of machine learning models that may be difficult or time consuming for a user to look through in order to select a particular machine learning model.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 2 illustrates an example introductory series of prompts.

FIG. 4 illustrates an example series of prompts related to dementia.

FIG. 5 illustrates an example series of prompts related to depression.

FIG. 6 illustrates an example series of prompts related to epilepsy.

DETAILED DESCRIPTION

Like reference numbers and designations in the various drawings indicate like elements.

This specification describes a system that can determine a subset of brain data of a patient that is clinically relevant for the patient. In this specification, a set of data is "clinically relevant" if the data can be presented as an answer to a question that a trained clinician might ask in clinical practice treating patients, e.g., a question asked by a clinician in order to treat a patient with a specific disease measured in the data.

For example, the system can determine a subset of brain data based at least in part on clinical observation input, where the clinical observation is of the individual whose brain data is in question. The system can determine the subset of data using responses to a series of prompts provided to a user, e.g., a clinician. The system can then present the subset of the brain data to the user in a graphical interface. In some implementations, the system can further determine one or more machine learning models for processing the determined subset of data to generate clinically-relevant model outputs.

Figure 1A:
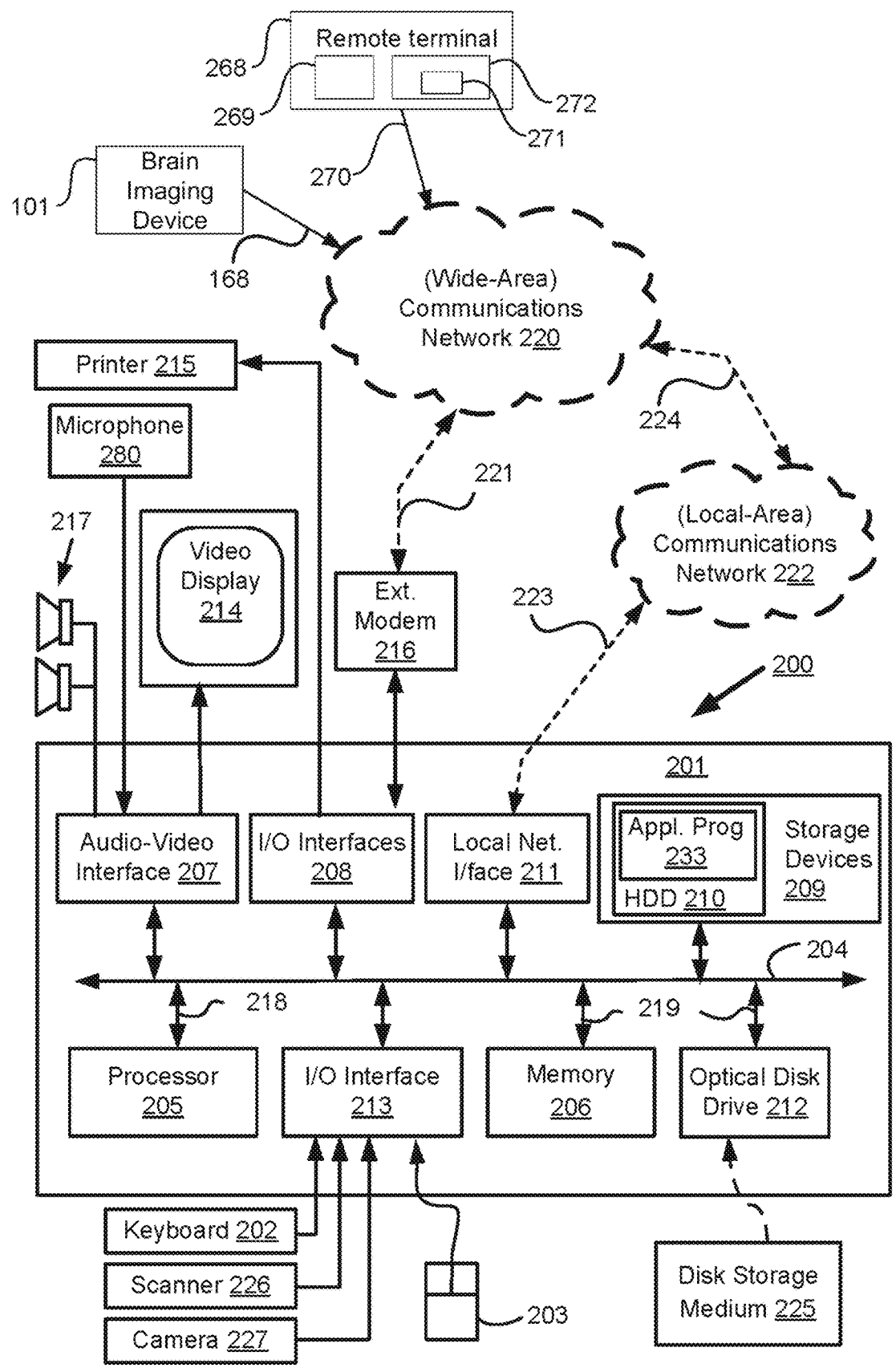
FIG. 1A and FIG. 1B are block diagrams that illustrate an example computer system.
Figure 1B:
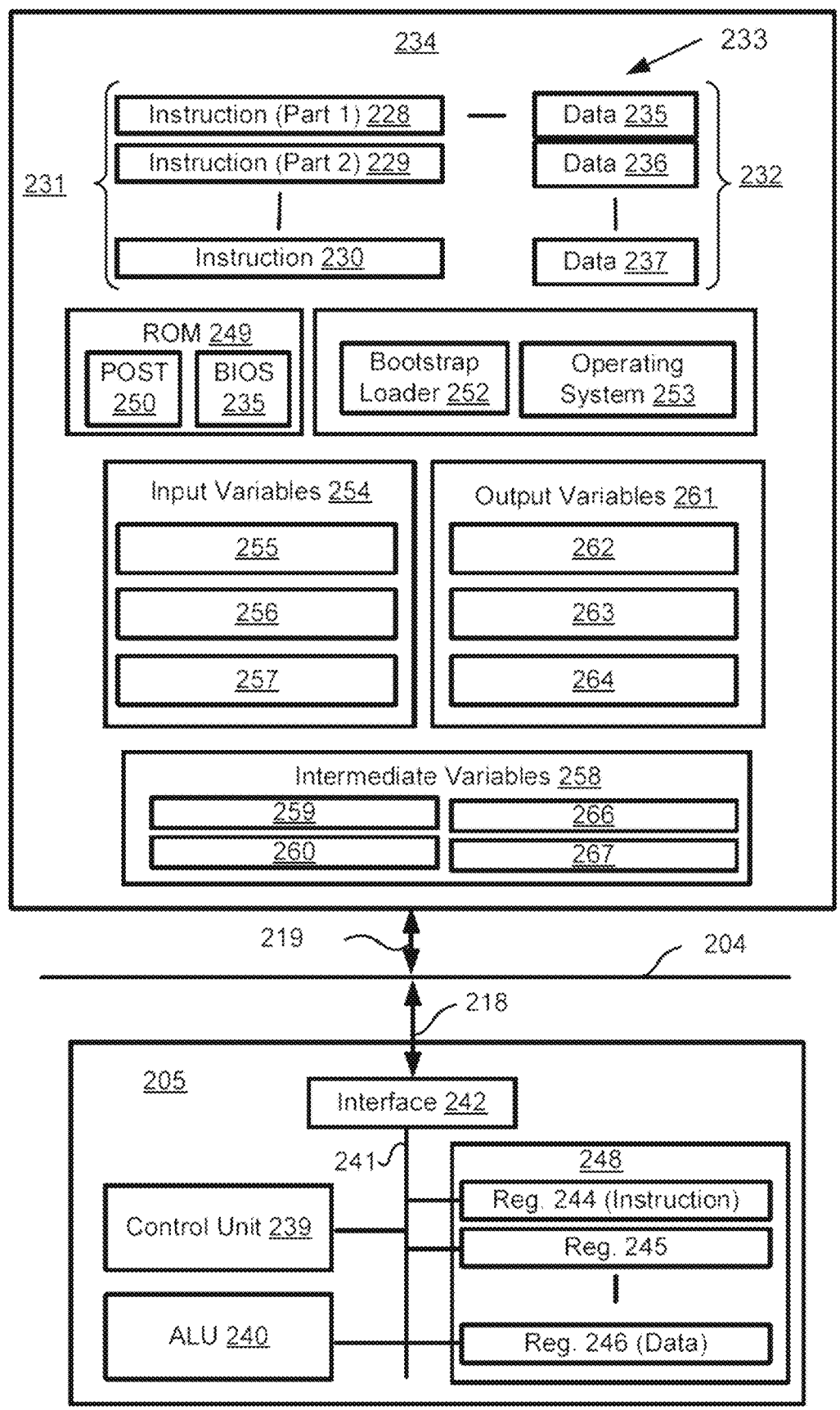

FIGS. 1A and 1B are block diagrams of a general-purpose computer system 200 upon which one can practice arrangements described in this specification. The following description is directed primarily to a computer server module 201. However, the description applies equally or equivalently to one or more remote terminals 268.

As seen in FIG. 1A, the computer system 200 includes: the server computer module 201; input devices such as a keyboard 202, a pointer device 203 (e.g., a mouse), a scanner 226, a camera 227, and a microphone 280; and output devices including a printer 215, a display device 214 and loudspeakers 217. An external Modulator-Demodulator (Modem) transceiver device 216 may be used by the computer server module 201 for communicating to and from the remote terminal 268 over a computer communications network 220 via a connection 221 and a connection 270. The aforementioned communication can take place between the remote terminal 268 and "the cloud" which in the present description comprises at least the one server module 201. The remote terminal 268 typically has input and output devices (not shown) which are similar to those described in regard to the server module 201. The communications network 220 may be a wide-area network (WAN), such as the Internet, a cellular telecommunications network, or a private WAN. Where the connection 221 is a telephone line, the modem 216 may be a traditional "dial-up" modem. Alternatively, where the connection 221 is a high capacity (e.g., cable) connection, the modem 216 may be a broadband modem. A wireless modem may also be used for wireless connection to the communications network 220.

The computer server module 201 typically includes at least one processor unit 205, and a memory unit 206. For example, the memory unit 206 may have semiconductor random access memory (RAM) and semiconductor read only memory (ROM). The remote terminal 268 typically includes as least one processor 269 and a memory 272. The computer server module 201 also includes a number of input/output (I/O) interfaces including: an audio-video interface 207 that couples to the video display 214, loudspeakers 217 and microphone 280; an I/O interface 213 that couples to the keyboard 202, mouse 203, scanner 226, camera 227 and optionally a joystick or other human interface device (not illustrated); and an interface 208 for the external modem 216 and printer 215. In some implementations, the modem 216 may be incorporated within the computer module 201, for example within the interface 208. The computer module 201 also has a local network interface 211, which permits coupling of the computer system 200 via a connection 223 to a local-area communications network 222, known as a Local Area Network (LAN). As illustrated in FIG. 1A, the local communications network 222 may also couple to the wide network 220 via a connection 224, which would typically include a so-called "firewall" device or device of similar functionality. The local network interface 211 may include an Ethernet circuit card, a Bluetooth® wireless arrangement or an IEEE 802.11 wireless arrangement; however, numerous other types of interfaces may be practiced for the interface 211.

The I/O interfaces 208 and 213 may afford either or both of serial or parallel connectivity; the former may be implemented according to the Universal Serial Bus (USB) standards and having corresponding USB connectors (not illustrated). Storage memory devices 209 are provided and typically include a hard disk drive (HDD) 210. Other storage devices such as a floppy disk drive and a magnetic tape drive (not illustrated) may also be used. An optical disk drive 212 is typically provided to act as a non-volatile source of data. Portable memory devices, such optical disks (e.g., CD-ROM, DVD, Blu ray Disc™), USB-RAM, portable, external hard drives, and floppy disks, for example, may be used as appropriate sources of data to the system 200.

The components 205 to 213 of the computer module 201 typically communicate via an interconnected bus 204 and in a manner that results in a conventional mode of operation of the computer system 200 known to those in the relevant art. For example, the processor 205 is coupled to the system bus 204 using a connection 218. Likewise, the memory 206 and optical disk drive 212 are coupled to the system bus 204 by connections 219.

The techniques described in this specification may be implemented using the computer system 200, e.g., may be implemented as one or more software application programs 233 executable within the computer system 200. In some implementations, the one or more software application programs 233 execute on the computer server module 201 (the remote terminal 268 may also perform processing jointly with the computer server module 201), and a browser 271 executes on the processor 269 in the remote terminal, thereby enabling a user of the remote terminal 268 to access the software application programs 233 executing on the server 201 (which is often referred to as "the cloud") using the browser 271. In particular, the techniques described in this specification may be effected by instructions 231 (see FIG. 1B) in the software 233 that are carried out within the computer system 200. The software instructions 231 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 200 from the computer readable medium, and then executed by the computer system 200. A computer readable medium having such software or computer program recorded on the computer readable medium is a computer program product.

Software modules for that execute techniques described in this specification may also be distributed using a Web browser.

The software 233 is typically stored in the HDD 210 or the memory 206 (and possibly at least to some extent in the memory 272 of the remote terminal 268). The software is loaded into the computer system 200 from a computer readable medium, and executed by the computer system 200. Thus, for example, the software 233, which can include one or more programs, may be stored on an optically readable disk storage medium (e.g., CD-ROM) 225 that is read by the optical disk drive 212. A computer readable medium having such software or computer program recorded on it is a computer program product.

In some instances, the application programs 233 may be supplied to the user encoded on one or more CD-ROMs 225 and read via the corresponding drive 212, or alternatively may be read by the user from the networks 220 or 222. Still further, the software can also be loaded into the computer system 200 from other computer readable media. Computer readable storage media refers to any non-transitory tangible storage medium that provides recorded instructions and/or data to the computer system 200 for execution and/or processing. Examples of such storage media include floppy disks, magnetic tape, CD-ROM, DVD, Blu-Ray™ Disc, a hard disk drive, a ROM or integrated circuit, USB memory, a magneto-optical disk, or a computer readable card such as a PCMCIA card and the like, whether or not such devices are internal or external of the computer module 201. Examples of transitory or non-tangible computer readable transmission media that may also participate in the provision of software, application programs, instructions and/or data to the computer module 201 include radio or infra-red transmission channels as well as a network connection to another computer or networked device, and the Internet or Intranets including e-mail transmissions and information recorded on Websites and the like.

The second part of the application programs 233 and the corresponding code modules mentioned above may be executed to implement one or more graphical user interfaces (GUIs) to be rendered or otherwise represented upon the display 214. For example, through manipulation of the keyboard 202 and the mouse 203, a user of the computer system 200 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 217 and user voice commands input via the microphone 280.

FIG. 1B is a detailed schematic block diagram of the processor 205 and a "memory" 234. The memory 234 represents a logical aggregation of all the memory modules (including the HDD 209 and semiconductor memory 206) that can be accessed by the computer module 201 in FIG. 1A.

When the computer module 201 is initially powered up, a power-on self-test (POST) program 250 can execute. The POST program 250 can be stored in a ROM 249 of the semiconductor memory 206 of FIG. 1A. A hardware device such as the ROM 249 storing software is sometimes referred to as firmware. The POST program 250 examines hardware within the computer module 201 to ensure proper functioning and typically checks the processor 205, the memory 234 (209, 206), and a basic input-output systems software (BIOS) module 251, also typically stored in the ROM 249, for correct operation. Once the POST program 250 has run successfully, the BIOS 251 can activate the hard disk drive 210 of FIG. 1A. Activation of the hard disk drive 210 causes a bootstrap loader program 252 that is resident on the hard disk drive 210 to execute via the processor 205. This loads an operating system 253 into the RAM memory 206, upon which the operating system 253 commences operation. The operating system 253 is a system level application, executable by the processor 205, to fulfil various high-level functions, including processor management, memory management, device management, storage management, software application interface, and generic user interface.

The operating system 253 manages the memory 234 (209, 206) to ensure that each process or application running on the computer module 201 has sufficient memory in which to execute without colliding with memory allocated to another process. Furthermore, the different types of memory available in the system 200 of FIG. 1A must be used properly so that each process can run effectively. Accordingly, the aggregated memory 234 is not intended to illustrate how particular segments of memory are allocated (unless otherwise stated), but rather to provide a general view of the memory accessible by the computer system 200 and how such is used.

As shown in FIG. 1B, the processor 205 includes a number of functional modules including a control unit 239, an arithmetic logic unit (ALU) 240, and a local or internal memory 248, sometimes called a cache memory. The cache memory 248 typically includes a number of storage registers 244-246 in a register section. One or more internal busses 241 functionally interconnect these functional modules. The processor 205 typically also has one or more interfaces 242 for communicating with external devices via the system bus 204, using a connection 218. The memory 234 is coupled to the bus 204 using a connection 219.

The application program 233 includes a sequence of instructions 231 that may include conditional branch and loop instructions. The program 233 may also include data 232 which is used in execution of the program 233. The instructions 231 and the data 232 are stored in memory locations 228, 229, 230 and 235, 236, 237, respectively. Depending upon the relative size of the instructions 231 and the memory locations 228-230, a particular instruction may be stored in a single memory location as depicted by the instruction shown in the memory location 230. Alternately, an instruction may be segmented into a number of parts each of which is stored in a separate memory location, as depicted by the instruction segments shown in the memory locations 228 and 229.

In general, the processor 205 is given a set of instructions which are executed therein. The processor 205 waits for a subsequent input, to which the processor 205 reacts to by executing another set of instructions. Each input may be provided from one or more of a number of sources, including data generated by one or more of the input devices 202, 203, data received from an external source 101, e.g., a brain imaging device 101 such such as an MRI or DTI scanner, across one of the networks 220, 202, data retrieved from one of the storage devices 206, 209 or data retrieved from a storage medium 225 inserted into the corresponding reader 212, all depicted in FIG. 1A. The execution of a set of the instructions may in some cases result in output of data. Execution may also involve storing data or variables to the memory 234.

Some techniques described in this specification use input variables 254, e.g., data sets characterizing the brain of a patient, which are stored in the memory 234 in corresponding memory locations 255, 256, 257. The techniques can produce output variables 261, which are stored in the memory 234 in corresponding memory locations 262, 263, 264. Intermediate variables 258 may be stored in memory locations 259, 260, 266 and 267.

Referring to the processor 205 of FIG. 1B, the registers 244, 245, 246, the arithmetic logic unit (ALU) 240, and the control unit 239 work together to perform sequences of micro-operations needed to perform "fetch, decode, and execute" cycles for every instruction in the instruction set making up the program 233. Each fetch, decode, and execute cycle can include i) a fetch operation, which fetches or reads an instruction 231 from a memory location 228, 229, 230; ii) a decode operation in which the control unit 239 determines which instruction has been fetched; and iii) an execute operation in which the control unit 239 and/or the ALU 240 execute the instruction.

Thereafter, a further fetch, decode, and execute cycle for the next instruction may be executed. Similarly, a store cycle may be performed by which the control unit 239 stores or writes a value to a memory location 232.

Each step or sub-process in the techniques described in this specification may be associated with one or more segments of the program 233 and is performed by the register section 244, 245, 247, the ALU 240, and the control unit 239 in the processor 205 working together to perform the fetch, decode, and execute cycles for every instruction in the instruction set for the noted segments of the program 233. Although a cloud-based platform has been described for practicing the techniques described in this specification, other platform configurations can also be used. Furthermore, other hardware/software configurations and distributions can also be used for practicing the techniques described in this specification.

Figure 7:
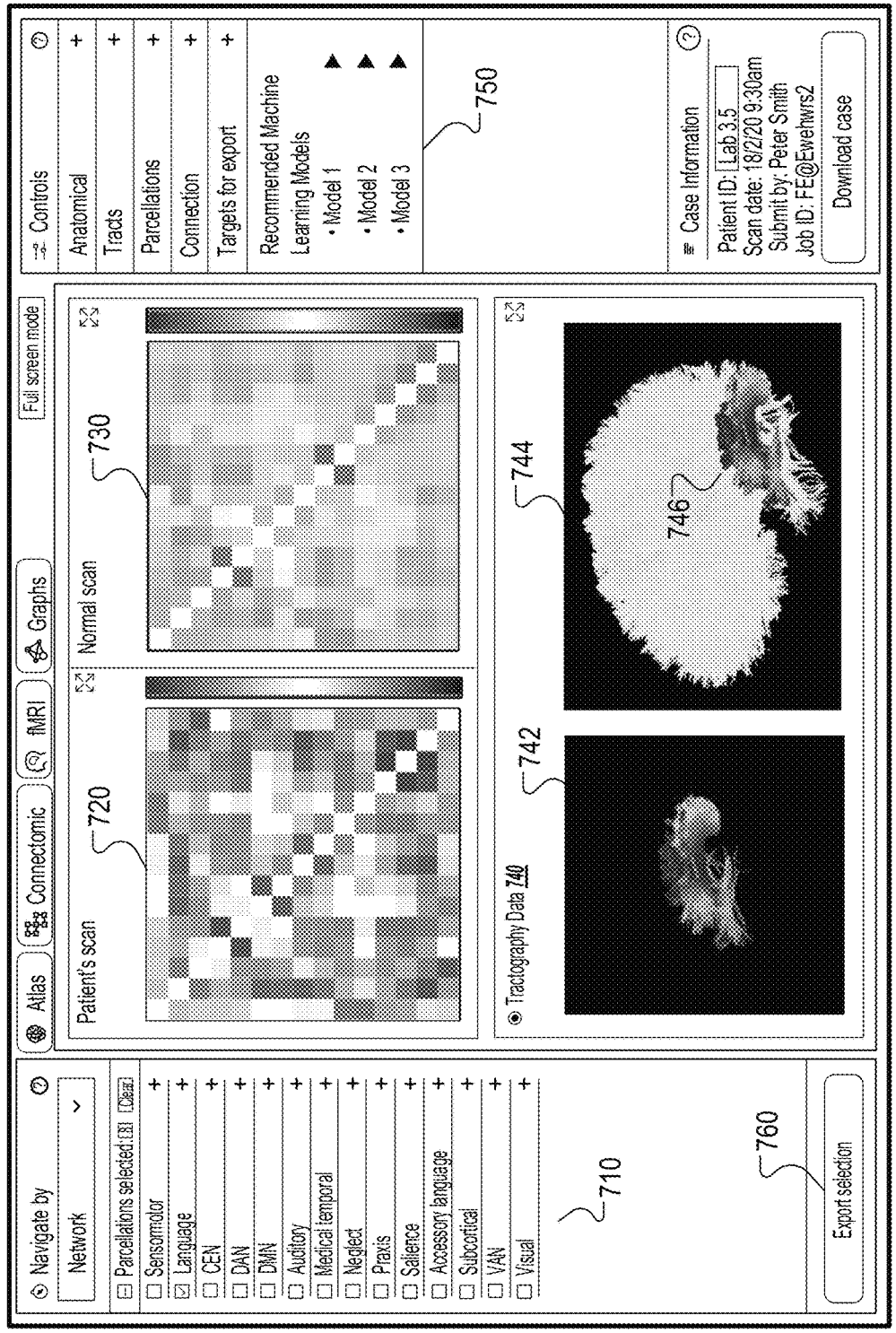
FIG. 7 illustrates an example graphical interface for presenting a subset of brain data.

FIGS. 2-6 illustrate example graphical interfaces for displaying prompts to a user for determining a subset of brain data of a patient that is clinically relevant to the patient. FIG. 7 illustrates an example graphical interface for displaying the subset of the brain data to the user. Data for each example graphical interface can be generated by a computer server module, e.g., the computer server module 201 depicted in FIG. 1A and then forwarded to a display or remote terminal. After graphical interface data is generated, the graphical interface can be presented to the user on a display device, e.g., on the display device 214 depicted in FIG. 1A. As described above, in some implementations the computer server module is in the same location as the display device, e.g., the computer server module and the display device can each be components of the same device. In some other implementations, the computer server module is remote, e.g., on the cloud.

In either case, the user can interact with the graphical interface in order to provide responses to the prompts displayed on the display device; for example, the user can provide one or more user inputs using keyboard, mouse, and/or microphone, e.g., the keyboard 202, mouse 203, and microphone 280 depicted in FIG. 1A. The user inputs can be provided to the computer server module, which can process the user inputs in order to process the brain data and/or generate a next graphical interface for the user.

For convenience, in the descriptions below of FIGS. 2-7, the graphical interfaces will be described as being generated and provided to the user by a "system," i.e., a system of one or more computers located in one or more locations. It is to be understood that the system can include the computer server module and the display device described above with reference to FIG. 1A.

In particular, given a particular sequence of prompts and responses, the system can determine either i) a next prompt to provide to the user, or ii) a subset of the brain data of the patient to provide to the user. In order to make this determination, the system can maintain a data model that defines, for every possible sequence of prompts and responses, either a next prompt or a particular subset of patient brain data. As a particular example, the system can maintain a tree structure, where each non-leaf node of the tree corresponds to a prompt, each branch of the tree corresponds to a particular response to a prompt, and each leaf node corresponds to a particular subset of patient brain data. When the system displays a first prompt to the user and receives back a response, the system can descend down the tree structure from the node corresponding to the first prompt, along the branch corresponding to the response, and to a second node corresponding to a second prompt. The system can continue traversing the tree until reaching a leaf node, at which time the system can end the series of prompts and determine a particular subset of the brain data of the patient. The system can use any appropriate data model to define how the system should proceed given a particular sequence of prompt responses.

While particular examples of prompts and series of prompts are presented in FIGS. 2-6, in general the system can present any prompt that might be relevant to generating a subset of the brain data of a patient. In particular, the prompts in a series of prompts can be presented in a different order than the example series of prompts that are depicted in FIGS. 2-6, and a series of prompts can include one or more prompts that are not depicted in FIGS. 2-6 at all.

FIG. 2 illustrates an example introductory series of prompts 290, 294, and 295.

The system can present the first prompt 290 to the user upon receiving a user input indicating that the user wishes to generate a new subset of the brain data of a patient. For example, the user might select an icon that corresponds to starting a new flow of prompts. In some implementations, the first prompt 290 can be preceded by a selection of a particular patient of whose brain data the user wishes to generate a subset. In some other implementations, the user is already examining data related to a particular patient when the user submits the user input that triggers the first prompt 290.

The first prompt 290 includes three options 291, 292, and 293 that the user may select. The first option 291 allows a user to immediately begin to analyze the brain data of the patient. That is, the subset of the data corresponding to the first option 291 is the entire set of brain data of the patient. This can be useful if the user does not know exactly what the user might be looking for, and wishes to analyze the brain data on a high level.

The second option 292 allows the user to plan a brain surgery, which triggers a series of one or more prompts related to planning the brain surgery. If the user selects the second option 292, then the system can generate and display the second prompt 294, discussed in more detail below.

The third option 293 allows the user to enter a "research mode," which triggers a series of one or more prompts related to particular brain diseases and mental disorders. In some implementations, the "research mode" includes techniques that are not yet approved by a regulatory agency. Some regulatory agencies allow some non-regulatory-approved techniques to be offered in applications to users as long as the techniques are in a clearly indicated "research mode" in the application. As a particular example, a machine learning model that processes brain data of a patient to generate a prediction of whether the patient has a particular brain disease may be provided to the user as a possibility if the user selects the third prompt 293 corresponding to the "research mode."

The second prompt 294, which can be displayed to the user in response to the user selecting the second option 292 of the first prompt 290, allows the user to select a particular region of the brain for which the patient might undergo surgery. Note that the regions of the brain depicted in FIG. 2 are exemplary only and are not intended to be an exhaustive list.

In some cases, when the user selects a region of the brain in response to the second prompt 294, the system ends the series of prompts and selects the subset of the brain data of the patient that corresponds to the selected region of the brain. The system can then display the determined subset of brain data to the user. This process is discussed in more detail below in reference to FIG. 7.

In some other cases, when the user selects a region of the brain, e.g., the lateral frontal region, the system can generate and display a new prompt that lists possible types of brain surgeries that can be performed in the selected region.

The third prompt 295, which can be displayed to the user in response to the user selecting the third option 293 of the first prompt 290, allows the user to select a particular brain disease or mental disorder. Note that the diseases depicted in FIG. 2 are exemplary only and are not intended to be an exhaustive list.

When the user selects a disease, the system can generate another prompt corresponding to the selected disease. FIGS. 3-6 each illustrate example series of prompts corresponding to respective selected diseases.

Figure 3:
FIG. 3 illustrates an example series of prompts related to brain tumors.

FIG. 3 illustrates an example series of prompts 310-330 related to brain tumors. That is, the system can generate and display the second prompt 320 in response to the user selecting the "brain tumor" option in the first prompt 310.

The second prompt 320 provides the user a list of options for proceeding. For example, if the user selects the "plan using machine learning" option, then the system can end the series of prompts and select one or more machine learning models related to brain tumors. As a particular example, a machine learning model can process a particular subset of the brain data of the user to generate a recommendation for a treatment, e.g., surgery or chemotherapy. In some implementations, the system can display the one or more machine learning models to the user in a graphical interface, and the user can select one or more of the machine learning models to be executed. In some other implementations, the system can automatically execute the one or more machine learning models and display the model outputs of the one or more machine learning models.

As another example, if the user selects the "plan using resting state" option, then the system can end the series of prompts and select a subset of the brain data that was gathered while the user was in a resting state, e.g., a resting state fMRI of the user. The system can further subset the resting state data according to clinical research or one or more machine learning models that determine which subset of resting state data is most informative with respect to brain tumors.

As another example, if the user selects the "study the connectome" option, then the system can end the series of prompts and select a subset of connectomics data in the brain data that is known to be related to brain tumors.

As another example, if the user selects the "study the graph" option, then the system can end the series of prompts, select a subset of data in the brain data that is known to be related to brain tumors, and process the subset of data using one or more graph-theoretic models. For example, the system can process the determined subset of data using machine learning models that represent the brain as a graph of nodes connected by edges and extract useful information using this representation.

As another example, if the user selects the "calculate a difference map" option, then the system can end the series of prompts, select a subset of the brain data related to brain tumors, and generate a difference map, which is a visual display of how connectomics features have changes over time. The system can then display the difference map to the user.

As another example, if the user selects the "select a neurological deficit" option, then the system can generate and display the third prompt 330 to the user. The third prompts lists possible neurological deficits that can be caused by a brain tumor. When the user selects one of the options, e.g., the "language" option, the system can end the series of prompts and determine a subset of the brain data that corresponds to the selected neurological deficit. That is, certain portions of the brain are known to relate to motor skills, language, vision, etc. Therefore, the system can determine the subset of the brain data that characterizes the region corresponding to the selected neurological deficit. The system can then display the determined subset of brain data to the user. This process is discussed in more detail below in reference to FIG. 7.

FIG. 4 illustrates an example series of prompts 410-420 related to dementia. That is, the system can generate and display the second prompt 420 in response to the user selecting the "dementia" option in the first prompt 410.

The second prompt 420 provides the user a list of options for proceeding. For example, if the user selects the "compare connectome to normal" option, then the system can end the series of prompts and determine a subset of connectomics data in the brain data of the patient that is known to be related to dementia. The system can also obtain a "normal" version of the determined connectomics data, e.g., an averaged version of the determined connectomics data corresponding to different patients that are known not to have dementia. The system can also select one or more machine learning algorithms that are trained to process connectomics data corresponding to a particular patient and generate a prediction of whether the particular patient has dementia, e.g., generate a value between 0 and 1 characterizing the likelihood that the particular patient has dementia.

As another example, if the user selects the "classify subtype" option, then the system can end the series of prompts and determine a subset of the brain data of the patient that is known to relate to one or more subtypes of dementia. The system can also select one or more machine learning algorithms that are trained to process brain data of a particular patient and generate a prediction of which subtype of dementia the patient might have.

As another example, if the user selects the "address a neurological deficit" option, then the system can generate and display a list of possible neurological deficits, as described above in reference to FIG. 3.

As another example, if the user selects the "study changes in the disease" option, then the system can end the series of prompts and determine i) a first subset of the brain data corresponding to a particular region of the brain and that was gathered at a first time point, and ii) a second subset of the brain data corresponding to the particular region of the brain and that was gathered at a second time point. That is, the two subsets of the brain data correspond to the same region of the brain at different time points, e.g., two images of the brain captured on two different dates. The system can display these subsets of data to the user, so that the user can compare the two subsets and determine a change over time.

Figure 5:
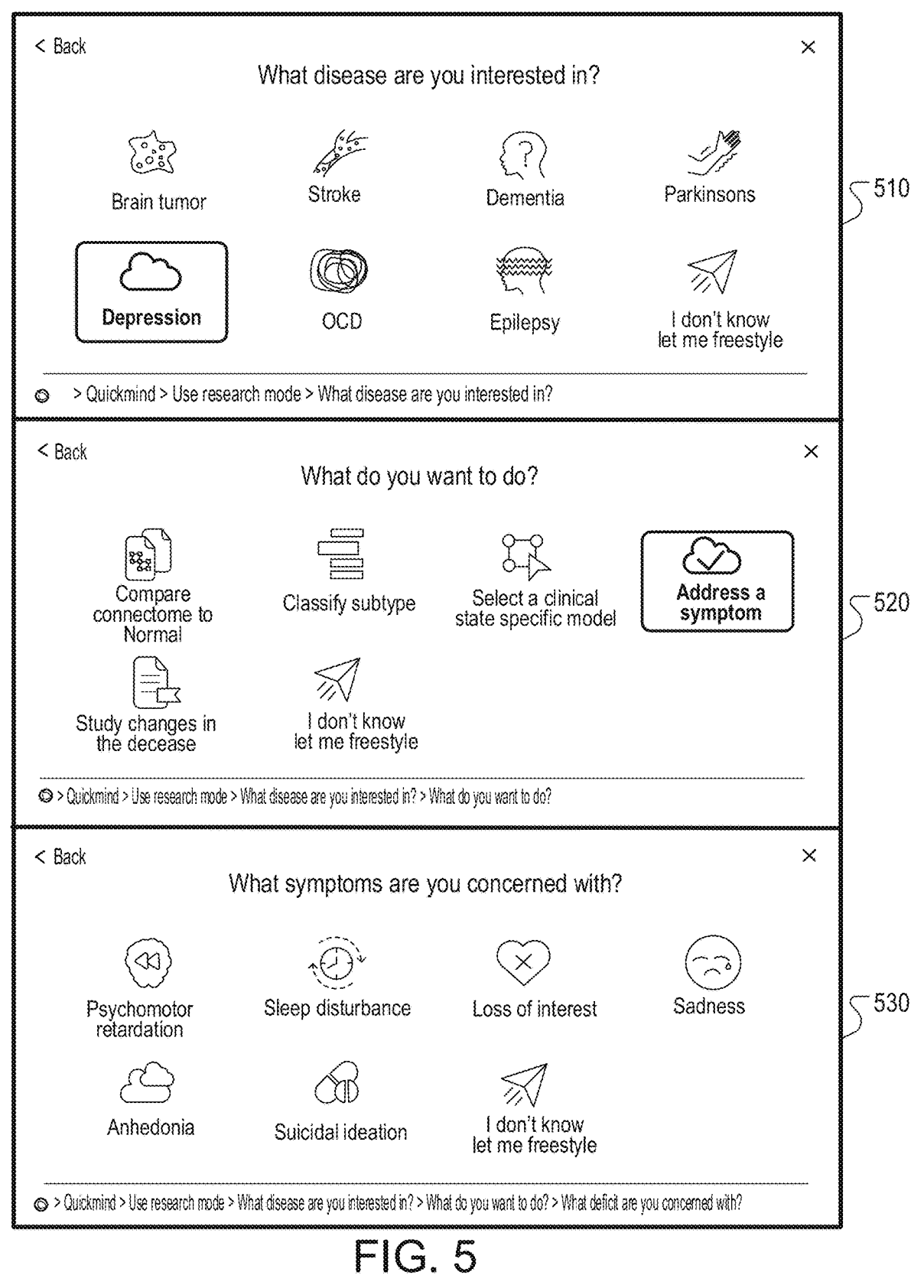

FIG. 5 illustrates an example series of prompts 510-530 related to depression. That is, the system can generate and display the second prompt 520 in response to the user selecting the "depression" option in the first prompt 510.

The second prompt 520 provides the user a list of options for proceeding. For example, if the user selects the "compare connectome to normal" option, then the system can end the series of prompts and determine a subset of connectomics data in the brain data of the patient that is known to be related to depression, as described above in reference to FIG. 4.

As another example, if the user selects the "classify subtype" option, then the system can end the series of prompts and determine a subset of the brain data of the patient that is known to relate to one or more subtypes of depression, as described above in reference to FIG. 4.

As another example, if the user selects the "select a clinical state specific model" option, then the system can display a new prompt to the user to select a particular machine learning model that will process the brain data. Each machine learning model can correspond to a particular clinical state, and can be trained to process a subset of the brain data of the patient that is known to relate to depression to generate a model output. For example, one or more of the machine learning models can be trained to determine how the patient might respond to a particular treatment, e.g., transcranial magnetic stimulation (TMS) or a particular medication. The system can then execute the selected machine learning model, and display the model outputs to the user.

As another example, if the user selects the "address a symptom" option, then the system can generate and display the third prompt 530 to the user. The third prompts lists possible symptoms that are associated with depression, e.g., psychomotor retardation, sleep disturbance, etc. When the user selects one of the symptoms, then the system can end the series of prompts and determine a subset of the brain data of the patient that is known to be related to depression, and in particular that is known to be related to the selected symptom.

FIG. 6 illustrates an example series of prompts 610-620 related to epilepsy. That is, the system can generate and display the second prompt 620 in response to the user selecting the "epilepsy" option in the first prompt 610.

The second prompt 620 provides the user a list of options for proceeding. For example, if the user selects the "find the focus" option, then the system can end the sequence of prompts, determine a subset of the brain data that is known to correspond to epilepsy, and process the determined subset of the brain data using a machine learning model that is trained to identify abnormalities in one or more regions of the brain that might suggest that the regions will be the onset zone of seizures in the patient. As a particular example, the machine learning model can be a convolutional neural network that processes connectomics data of a patient to identify abnormalities in one or more regions.

As another example, if the user selects the "determine what was removed" option, then the system can end the sequence of prompts, select a subset of the brain data related to epilepsy, and generate a difference map characterizing how the subset of brain data has changed over time. For example, the system can determine a first subset of the brain data that was obtained before an operation and a second subset of the brain data that was obtained after the operation, and generate a difference map characterizing the change in the brain data caused by the operation. FIG. 7 illustrates an example graphical interface 700 for presenting a subset of brain data of a patient. The subset of the brain data of the patient was determined by the system according to a sequence of prompts provided to a user and responses to the prompts obtained from the user. The graphical interface 700 can be displayed to the user after the final prompt.

The graphical interface 700 includes a list 710 of the regions of the brain, with the regions that correspond to the determined subset of the brain data selected. In the example depicted in FIG. 7, the "language" region is selected because the determined subset of the brain data includes data corresponding to the language region of the brain. As a particular example, the system can generate the graphical interface 700 and display it to the user in response to the user selecting the "language" option to the third prompt 330 depicted in FIG. 3.

The other regions of the brain listed in the list 710 that are not selected each have a corresponding graphical element, depicted as an empty box, that the user can select. When the user selects a new region, the system can add data corresponding to the region to the subset of the brain data and re-generate the graphical interface 700 to reflect the augmented subset of the brain data.

The graphical interface 700 includes a correlation matrix 720 that is a part of the determined subset of the brain data of the patient. A correlation matrix can be generated from the brain functional connectivity data of a patient, and displays the correlation between areas of the brain of the patient. In particular, for an element of a correlation matrix in a row that corresponds to a first area of the brain and in a column that corresponds to a second region of the brain, the value of the element characterizes the correlation between the first area and the second area. The value of each element can be represented by a different color.

The correlation matrix 720 corresponds to the language region of the brain of the patient. The interface 700 also includes a correlation matrix 730 corresponding to a "normal" scan. For example, as described above, the "normal" correlation matrix 730 can be an averaged version of the correlation matrices of multiple different patients that are known to have healthy language regions of the brain. The patient's correlation matrix 720 and the normal correlation matrix 730 are presented side-by-side so that the user can easily compare them.

The graphical interface 700 includes a three-dimensional model 740 of diffusion tractography data corresponding to a determined subset of the brain data. In some implementations, the system only renders the tracts 742 corresponding to the determined subset. Instead or in addition, the system can render the tracts 744 of the whole brain, and emphasize or highlight the tracts 746 corresponding to the determined subset, e.g., using a particular color.

The graphical interface 700 includes a list of selected machine learning models 750 that correspond to the determined subset of the brain data of the patient. As described above, the system can select the machine learning models either using the same series of prompts by which the system determined the subset of brain data or via additional prompts. The selected machine learning models are clinically-relevant to the patient, according to the responses to the prompts.

As a particular example, a selected machine learning model can be trained to process the subset of data corresponding to the language region of the brain and generate a prediction of whether the patient has one or more diseases in the language region of the brain, e.g., Alzheimer's. As another particular example, a selected machine learning model can be trained to process the subset of data and generate a prediction of whether the patient will respond to a particular treatment or drug. As another particular example, a selected machine learning model can be trained to process the subset of data and prediction of one or more regions within the brain that might be an epilepsy zone. As another particular example, a selected machine learning model can be trained to process the subset of data and generate a prediction of one or more regions within the brain that might be affected by psychomotor retardation.

The machine learning models can each be trained to receive a model input that includes, at least a portion of the determined subset of the brain data, and process the model input to generate a model output. For example, one or more of the machine learning models can be trained to receive a model input that is exactly equal to the determined subset of the brain data, while one or more of the machine learning models can be trained to receive a model input that includes i) only a portion of the determined subset of the brain data and ii) a different subset of the brain data.

Each of the selected machine learning models in the list 750 have a corresponding graphical element, depicted as an arrow, that the user can select. When the user selects a machine learning model, the system can execute the machine learning model to generate a model output, and display the model output to the user.

The graphical interface 700 includes an "Export selection" option 760 that allows the user to export the determined subset of the brain data of the patient. That is, if the user selects the option 760, then the system can compile the determined subset of the data into a single file and provide the file to the user for download. Downloading the entire set of brain data of the user for further analysis can be intractable, as the amount of data can be too large for practical use; however, downloading only the relevant subset of the brain data, as determined by the clinically-relevant questions described above, can be more manageable and allow a user to further process the data.

As a particular example, a database that includes the brain data of the patient can have a data item, e.g., a tensor, that identifies three-dimensional coordinates of each parcellation in the brain data of the patient, e.g., (x,y,z) coordinates in a common coordinate space of the brain data of the patient. The database can also include a data item, e.g., a tensor, that identifies three-dimensional coordinate of each tract in the brain data of the patient, e.g., (x,y,z) coordinates in the common coordinate space. When exporting the determined subset of the brain data, the system can determine which data items to include in the exported file using the respective (x,y,z) coordinates. In the example depicted in FIG. 7, the system can determine a region in the common coordinate system, e.g., a set of (x,y,z) coordinates in the common coordinate system, that corresponds to the "language region" of the brain. The system can then determine which data points have (x,y,z) coordinates that are within the defined region, and select those data points to include in the exported file.

Figure 8:
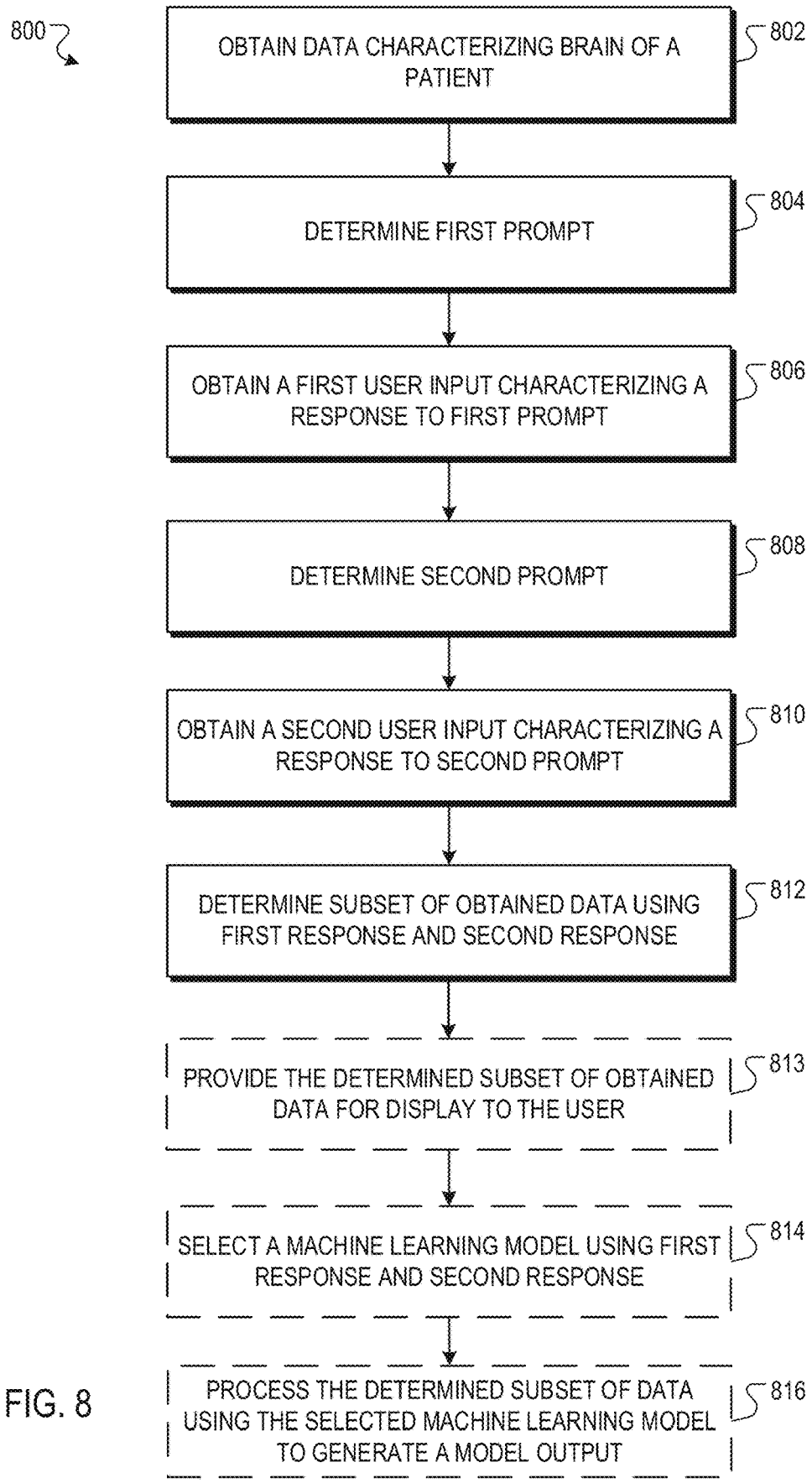
FIG. 8 is a flowchart of an example process for determining a subset of brain data.

FIG. 8 is a flowchart of an example process 800 for determining a subset of brain data. The process 800 can be implemented by one or more computer programs installed on one or more computers and programmed in accordance with this specification. For example, the process 800 can be performed by the computer server module depicted in FIG. 1A. For convenience, the process 800 will be described as being performed by a system of one or more computers.

The system obtains data characterizing the brain of a patient (step 802). The obtained data can include connectomics data of the brain of the patient. For example, the connectomics data can include a connectivity matrix that include multiple columns and rows corresponding to different regions of the brain.

The system determines a first prompt (step 804). For example, the first prompt can be a prompt to select a brain region, a prompt to select a disease, a prompt to select symptoms of the patient, or a prompt to select a neurological deficit. The system can provide the first prompt for display to the user, with one or more options for the user to respond.

The system obtains a first user input characterizing a response to the first prompt (step 806).

The system determines a second prompt (step 808). The system can determine the second prompt according to the response to the first prompt. As described above, the second prompt can be a prompt to select a brain region, a prompt to select a disease, a prompt to select symptoms of the patient, or a prompt to select a neurological deficit. The system can provide the second prompt for display to the user, with one or more options for the user to respond.

The system obtains a second user input characterizing a response to the second prompt (step 810). Either or both of the response to the first prompt or the response to the second prompt can seek a response based on a clinical observation of the patient.

The system determines a subset of the obtained data using the responses to the first prompt and the second prompt (step 812). The subset of the obtained data can include a subset of the connectivity matrix, i.e., a subset of the columns and rows.

Optionally, system provides the determined subset of the obtained data for display to the user (step 813). The system can display the determined subset to the user using a graphical interface. The graphical interface can include one or more user options to change the subset of the obtained data displayed on the graphical interface. That is, if the user selects one of these options, the system can display a different subset of the obtained data. The graphical interface can also include one or more user options to select a respective machine learning model. That is, if the user selects one of these options, the system can execute the corresponding machine learning model to generate a model output.

Optionally, the system selects a machine learning model using the first response and the second response (step 814). The machine learning model can be configured through training to process brain data, e.g., connectomics data, to generate a model output.

Optionally, the system processes at least a portion of the determined subset of the obtained data using the selected machine learning model to generate a model output (step 816). For example, the model output can characterize a likelihood that the patient has a particular disease.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g., a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method comprising:
obtaining data characterizing a brain of a patient;
determining a first prompt for presentation to a user;
obtaining a first user input characterizing a first response to the first prompt;
determining, using the first response to the first prompt, a second prompt for presentation to the user;
obtaining a second user input characterizing a second response to the second prompt, wherein at least one of the first prompt or the second prompt seek a response based on a clinical observation of the patient; and
determining a subset of the obtained data using the first response to the first prompt and the second response to the second prompt.

Embodiment 2 is the method of embodiment 1, wherein the obtained data comprises connectomics data.

Embodiment 3 is the method of embodiment 2, wherein the connectomics data comprises a connectivity matrix comprising a plurality of columns and rows.

Embodiment 4 is the method of embodiment 3, wherein the subset of the obtained data comprises a subset of the plurality of columns and rows of the connectivity matrix.

Embodiment 5 is the method of any one of embodiments 1-4, wherein one or more of the first prompt or the second prompt are one of:
a prompt to select a brain region;
a prompt to select a disease;
a prompt to select symptoms of the patient; or
a prompt to select a neurological deficit.

Embodiment 6 is the method of any one of embodiments 1-5, further comprising selecting, from the first response to the first prompt and the second response to the second prompt, one or more machine learning models, wherein each machine learning model has been configured through training to process data characterizing a brain of a patient and generate a model output.

Embodiment 7 is the method of embodiment 6, wherein the respective model output of one or more of the machine learning models characterizes a likelihood that the patient has a particular disease.

Embodiment 8 is the method of any one of embodiments 1-7, further comprising providing the determined subset of the obtained data for display to the user on a graphical interface.

Embodiment 9 is the method of embodiment 8, wherein the graphical interface comprises one or more of:
one or more user options to change the subset of the obtained data displayed on the graphical interface, or
one or more options to select a respective machine learning model.

Embodiment 10 is the method of any one of embodiments 1-9, further comprising generating a prediction of a health status of the patient according to the determined subset of the obtained data.

Embodiment 11 is a system comprising one or more computers and one or more storage devices storing instructions that are operable, when executed by the one or more computers, to cause the one or more computers to perform the method of any one of embodiments 1-10.

Embodiment 12 is a computer storage medium encoded with a computer program, the program comprising instructions that are operable, when executed by data processing apparatus, to cause the data processing apparatus to perform the method of any one of embodiments 1-10.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

What is claimed is:
1. A method comprising:
obtaining, by a system of one or more computers, brain data characterizing a brain of a single individual under examination, wherein the brain data represents a plurality of regions of the brain of the single patient;
determining a first prompt for presentation to a user;
providing the first prompt for display to the user;

obtaining a first user input characterizing a first response to the first prompt;

determining, based on the first response to the first prompt, a second prompt for presentation to the user;

providing the second prompt for display to the user;

obtaining a second user input characterizing a second response to the second prompt, wherein at least one of the first prompt or the second prompt requires the user to provide an indication of a health status of the single individual;

selecting, automatically by the system of one or more computers and using the first user input and the second user input, a proper subset of the brain data of the single individual, wherein the proper subset of the brain data represents a proper subset of the plurality of regions of the brain of the single individual, and wherein the proper subset of the brain data is based at least in part on the indication of the health status of the single individual for a condition;

in response to the automatic selection using the first user input and the second user input, obtaining, automatically by the system of computers, the proper subset of the brain data representing the proper subset of the plurality of regions without obtaining non-selected portions of the brain data characterizing the brain of the individual under examination, wherein the proper subset of the brain data is not more than $1/100^{th}$ the size of the brain data;

providing the obtained proper subset of the brain data representing the proper subset of the plurality of regions of the brain of the single individual for display to the user, wherein the proper subset of the brain data is displayed in an interface without displaying the non-selected portions of the brain data in the interface, wherein the brain data displayed comprises a patient connectivity matrix and a normal connectivity matrix, each connectivity matrix comprising a plurality of columns and rows, wherein each column and each row corresponds to a respective region of the brain, the normal connectivity matrix being a function of the connectivity matrices of patients that are known not to have the condition, each connectivity matrix having at least 200 elements;

selecting, in response to the first user input and the second user input, one or more machine learning models, wherein each machine learning model has been configured through training to process first brain data characterizing a brain of a first single patient and generate a model output representing a prediction about the brain of the first single individual and processing the obtained proper subset of data using the selected machine learning model to generate a model output.

2. The method of claim 1, wherein the brain data comprises connectomics data, the connectomics data comprising:

for each pair of regions comprising a first region and a second region from a plurality of regions of the brain of the single patient, a degree of correlation between brain activity in the first region and brain activity in the second region.

3. The method of claim 2, wherein the connectomics data comprises data representing a connectivity matrix comprising a plurality of columns and rows, wherein each column and each row corresponds to a respective region of the brain of the single patient.

4. The method of claim 2, wherein the connectomics data comprises data representing a connectivity matrix comprising a plurality of columns and rows, and wherein the proper subset of the brain data comprises a proper subset of the plurality of columns and rows of the connectivity matrix.

5. The method of claim 1, wherein one or more of the first prompt or the second prompt are one of:
 a prompt to select a brain region;
 a prompt to select a disease of the single patient;
 a prompt to select one or more symptoms of the single patient; or
 a prompt to select a neurological deficit of the single patient.

6. The method of claim 1, further comprising selecting, in response to the first user input and the second user input, one or more machine learning models, wherein each machine learning model has been configured through training to process first brain data characterizing a brain of a first single patient and generate a model output representing a prediction about the brain of the first single patient.

7. The method of claim 6, wherein the respective model outputs generated by one or more of the machine learning models characterize a likelihood that the single patient has a particular disease.

8. The method of claim 1, wherein displaying the proper subset of the brain data in the interface comprises displaying one or more of:
 one or more user options to change the proper subset of the brain data, or
 one or more user options to select a machine learning model for processing the proper subset of the brain data.

9. The method of claim 1, further comprising generating a prediction about the health status of the single patient using the proper subset of the brain data.

10. The method of claim 1, wherein determining the proper subset of the brain data characterizing the at least one specified network of the brain of the single patient comprises:
 determining coordinates, in a three-dimensional coordinate system of the brain of the single patient, of the at least one specified network; and
 identifying one or more elements of the brain data that correspond to the determined coordinates.

11. The method of claim 1, wherein:
 displaying the proper subset of the brain data in the interface comprises displaying a depiction of brain tracts of the at least one specified network of the brain of the single patient, the depiction being generated from the proper subset of the brain data.

12. A system comprising one or more computers and one or more storage devices storing instructions that are operable, when executed by the one or more computers, to cause the one or more computers to perform operations comprising:

Obtaining, by a system of one or more computers, brain data characterizing a brain of a single individual under examination, wherein the brain data represents a plurality of regions of the brain of the single patient;

determining a first prompt for presentation to a user;

providing the first prompt for display to the user;

obtaining a first user input characterizing a first response to the first prompt;

determining, based on the first response to the first prompt, a second prompt for presentation to the user;

providing the second prompt for display to the user;

obtaining a second user input characterizing a second response to the second prompt, wherein at least one of the first prompt or the second prompt requires the user to provide an indication of a health status of the single individual;

selecting, automatically by the system of one or more computers and using the first user input and the second user input, a proper subset of the brain data of the single individual, wherein the proper subset of the brain data represents a proper subset of the plurality of regions of the brain of the single individual, and wherein the proper subset of the brain data is based at least in part on the indication of the health status of the single individual for a condition;

in response to the automatic selection using the first user input and the second user input, obtaining, automatically by the system of computers, the proper subset of the brain data representing the proper subset of the plurality of regions without obtaining non-selected portions of the brain data characterizing the brain of the individual under examination, wherein the proper subset of the brain data is not more than $\frac{1}{100}^{th}$ the size of the brain data;

providing the obtained proper subset of the brain data representing the proper subset of the plurality of regions of the brain of the single individual for display to the user, wherein the proper subset of the brain data is displayed in an interface without displaying the non-selected portions of the brain data in the interface, wherein the brain data displayed comprises a patient connectivity matrix and a normal connectivity matrix, each connectivity matrix comprising a plurality of columns and rows, wherein each column and each row corresponds to a respective region of the brain, the normal connectivity matrix being a function of the connectivity matrices of patients that are known not to have the condition, each connectivity matrix having at least 200 elements;

selecting, in response to the first user input and the second user input, one or more machine learning models, wherein each machine learning model has been configured through training to process first brain data characterizing a brain of a first single patient and generate a model output representing a prediction about the brain of the first single individual and processing the obtained proper subset of data using the selected machine learning model to generate a model output.

13. The system of claim 12, wherein:

the brain data comprises connectomics data, the connectomics data comprising:

for each pair of regions comprising a first region and a second region from a plurality of regions of the brain of the single patient, a degree of correlation between brain activity in the first region and brain activity in the second region.

14. The system of claim 12, wherein one or more of the first prompt or the second prompt are one of:

a prompt to select a brain region;
a prompt to select a disease of the single patient;
a prompt to select one or more symptoms of the single patient; or
a prompt to select a neurological deficit of the single patient.

15. The system of claim 12, wherein the operations further comprise selecting, in response to the first user input and the second user input, one or more machine learning models, wherein each machine learning model has been configured through training to process first brain data characterizing a brain of a first single patient and generate a model output representing a prediction about the brain of the first single patient.

16. One or more non-transitory storage media storing instructions that when executed by one or more computers cause the one or more computers to perform operations comprising:

Obtaining, by a system of one or more computers, brain data characterizing a brain of a single individual under examination, wherein the brain data represents a plurality of regions of the brain of the single patient;

determining a first prompt for presentation to a user;
providing the first prompt for display to the user;
obtaining a first user input characterizing a first response to the first prompt;
determining, based on the first response to the first prompt, a second prompt for presentation to the user;
providing the second prompt for display to the user;
obtaining a second user input characterizing a second response to the second prompt, wherein at least one of the first prompt or the second prompt requires the user to provide an indication of a health status of the single individual;

selecting, automatically by the system of one or more computers and using the first user input and the second user input, a proper subset of the brain data of the single individual, wherein the proper subset of the brain data represents a proper subset of the plurality of regions of the brain of the single individual, and wherein the proper subset of the brain data is based at least in part on the indication of the health status of the single individual for a condition;

in response to the automatic selection using the first user input and the second user input, obtaining, automatically by the system of computers, the proper subset of the brain data representing the proper subset of the plurality of regions without obtaining non-selected portions of the brain data characterizing the brain of the individual under examination, wherein the proper subset of the brain data is not more than $\frac{1}{100}^{th}$ the size of the brain data;

providing the obtained proper subset of the brain data representing the proper subset of the plurality of regions the brain of the single individual for display to the user, wherein the proper subset of the brain data is displayed in an interface without displaying the non-selected portions of the brain data in the interface wherein the brain data displayed comprises a patient connectivity matrix and a normal connectivity matrix, each connectivity matrix comprising a plurality of columns and rows, wherein each column and each row corresponds to a respective region of the brain, the normal connectivity matrix being a function of the connectivity matrices of patients that are known not to have the condition, each connectivity matrix having at least 200 elements;

selecting, in response to the first user input and the second user input, one or more machine learning models, wherein each machine learning model has been configured through training to process first brain data characterizing a brain of a first single patient and generate a model output representing a prediction about the brain of the first single individual and processing the obtained proper subset of data using the selected machine learning model to generate a model output.

17. The non-transitory storage media of claim 16, wherein:
the brain data comprises connectomics data, the connectomics data comprising:
for each pair of regions comprising a first region and a second region from a plurality of regions of the brain of the single patient, a degree of correlation between brain activity in the first region and brain activity in the second region.

18. The non-transitory storage media of claim 16, wherein one or more of the first prompt or the second prompt are one of:
a prompt to select a brain region;
a prompt to select a disease of the single patient;
a prompt to select one or more symptoms of the single patient; or
a prompt to select a neurological deficit of the single patient.

19. The non-transitory storage media of claim 16, wherein the operations further comprise selecting, in response to the first user input and the second user input, one or more machine learning models, wherein each machine learning model has been configured through training to process first brain data characterizing a brain of a first single patient and generate a model output representing a prediction about the brain of the first single patient.

\* \* \* \* \*